(12) United States Patent
Kumar et al.

(10) Patent No.: US 8,216,843 B2
(45) Date of Patent: Jul. 10, 2012

(54) ARTIFICIALLY SYNTHESIZED PEPTIDE

(75) Inventors: Satish Kumar, Bareilly (IN); Manish Virendrasingh Bais, Bareilly (IN); Ranjit Singh Kataria, Bareilly (IN); Mahendra Pal Yadav, Bareilly (IN)

(73) Assignee: Indian Council of Agricultural Research, New Delhi (IN)

( * ) Notice: Subject to any disclaimer, the term of this patent is extended or adjusted under 35 U.S.C. 154(b) by 350 days.

(21) Appl. No.: 12/311,554

(22) PCT Filed: Oct. 6, 2006

(86) PCT No.: PCT/IB2006/002786
§ 371 (c)(1),
(2), (4) Date: Jan. 28, 2010

(87) PCT Pub. No.: WO2008/041047
PCT Pub. Date: Apr. 10, 2008

(65) Prior Publication Data
US 2011/0065175 A1    Mar. 17, 2011

(51) Int. Cl.
*C12N 15/00* (2006.01)
*C12N 5/00* (2006.01)
*A61K 38/00* (2006.01)

(52) U.S. Cl. .................. 435/455; 435/320.1; 435/325; 530/324

(58) Field of Classification Search .......... None
See application file for complete search history.

(56) References Cited

OTHER PUBLICATIONS

Elliott et al., "Intercellular trafficking and protein delivery by a herpesvirus structural protein" *Cell* 88:223-33, 1997.
Frankel et al., "Cellular uptake of Tat protein from human immunodeficiency virus" *Cell* 55:1189-93, 1988.
Schwarze et al., "In vivo protein transduction: delivery of biologically active protein into the mouse" *Science* 285:1569-72, 1999.
Lombardo et al., "VP5, the nonstructural polypeptide of infectious bursal disease virus, accumulates within the host plasma membrane and induces cell lysis" *Virology* 277(2):345-57, 2000.
Byrnes et al., "A nuclear targeting peptide, M9, improves transfection efficiency in fibroblasts" *J. Surg. Res.* 108(1):85-90, 2002.
Chevalier et al., "Structural peptides of a nonenveloped virus are involved in assembly and membrane translocation" *J. Virol.* 79(19):12253-63, 2005.
International Search Report for PCT/IB2006/002786, mailed Jul. 12, 2007.
International Preliminary Report on Patentability for PCT/IB2006/002786, issued Apr. 7, 2009.

*Primary Examiner* — Janet Epps-Smith
(74) *Attorney, Agent, or Firm* — Greenblum & Bernstein, P.L.C.

(57) ABSTRACT

A short synthetic vector peptide of 25 residues has been developed comprising hydrophobic domain and a novel, nuclear localization signal for efficient delivery, devoid of any cytotoxicity. Using the vector peptide, the oligonucleotide/peptide complexes got delivered evenly in cytoplasm and nucleus in less than an hour and finally localizing completely into nucleus in two hours and protein (antibody) to cytoplasm within 1 hour in both primary (chicken embryo fibroblast) cells and established mammalian cell line (Vero cells).

20 Claims, 2 Drawing Sheets

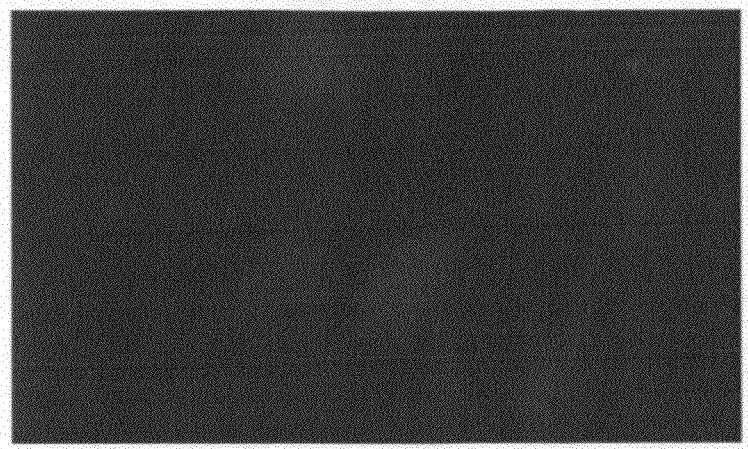

Fig. 1: Vero cell transfected with FITC labeled IgG antibody without peptide for 1 hr as a control.

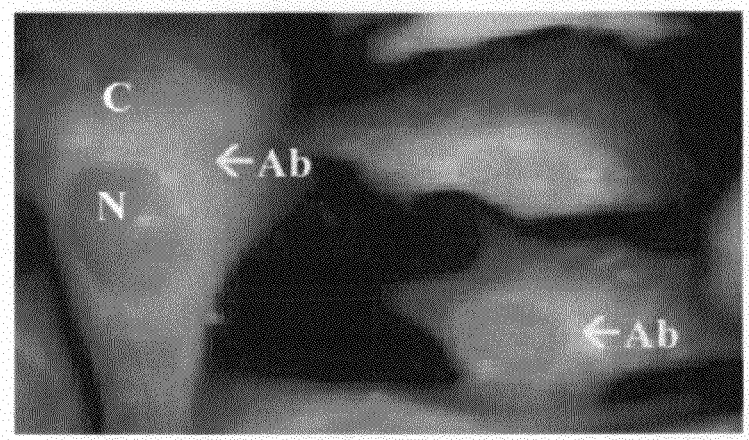

Fig. 2: Vero cells transfected with FITC labeled IgG antibody in presence of vector peptide for 1 hr indicates cytoplasmic (C) localization of antibody (Ab).

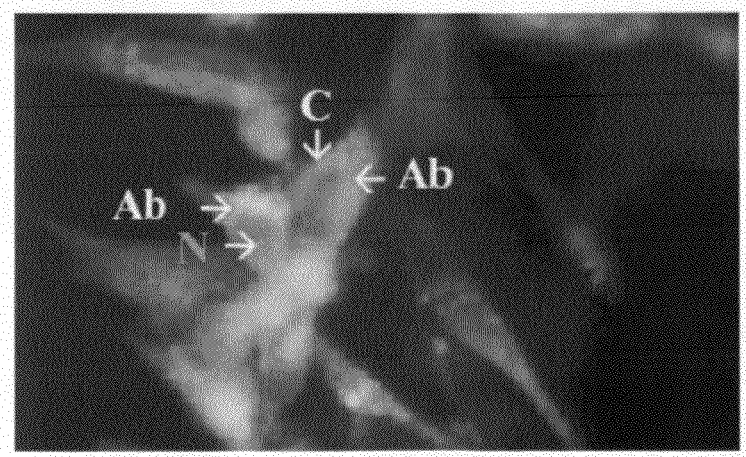

Fig. 3: Chicken embryo fibroblast cells transfected with FITC conjugated IgG antibody (Ab) complexed with vector peptide for 1 hr shows cytoplasmic (C) localization.

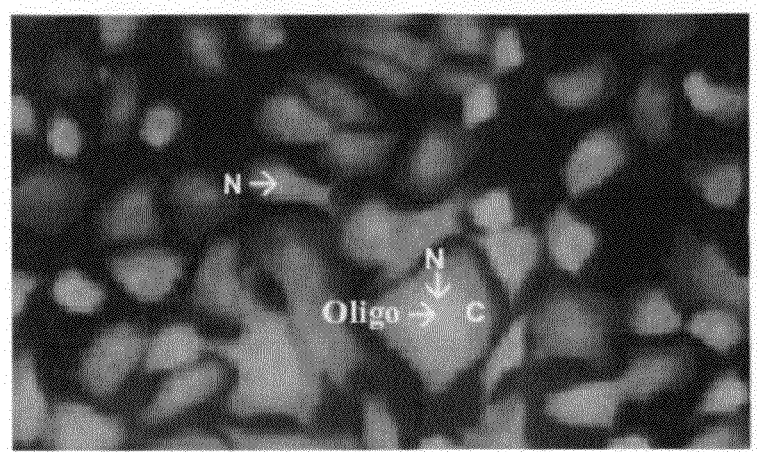

Fig. 4: Targeting FITC labelled oligonucleotides (oligo) complexed with vector peptide to nucleus of vero cells completely within 2 hrs.

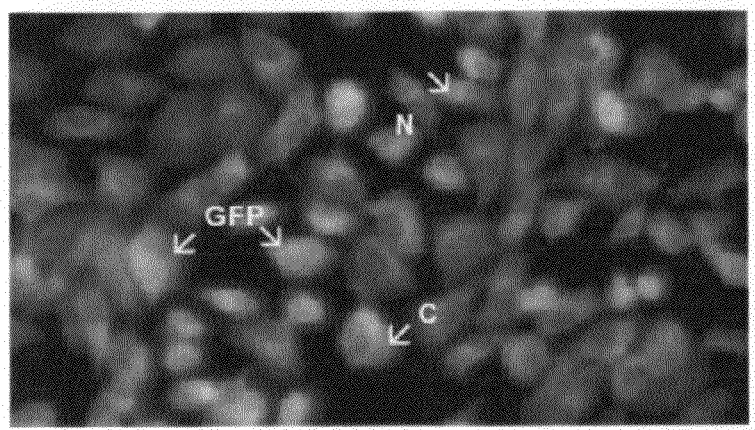

Fig. 5: Delivery of vector peptide mediated recombinant GFP reporter plasmid construct to vero cell showed efficient expression of green fluorescent protein (GFP) after 48 hrs in cytoplasm of vero cells

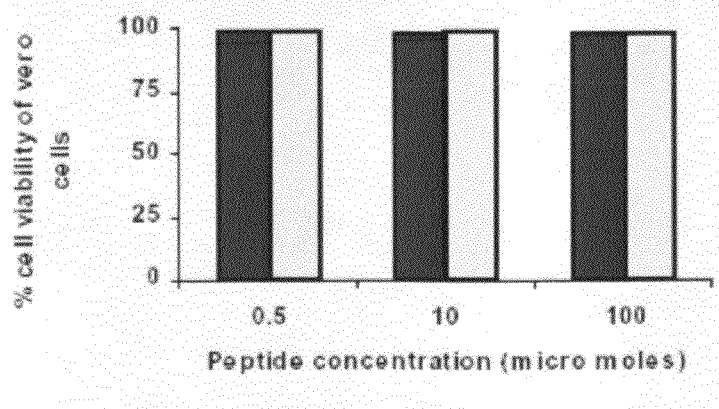

Fig. 6: Percent cell viability of complexes composed of peptide: antibody and peptide: GFP plasmid after 20 hrs of transfection.

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      25mer amino acid, wherein, modification was introduced in between
      C-terminal hydrophilic and N-terminal hydrophobic domain of
      22-mer peptide

<400> SEQUENCE: 1

Thr Pro Trp Trp Arg Leu Trp Thr Lys Trp Ser Gln Pro His His Lys
1               5                   10                  15

Arg Arg Asp Leu Pro Arg Lys Pro Glu
            20                  25

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      22-mer peptide corresponding to non structural protein of IBDV

<400> SEQUENCE: 2

Thr Pro Trp Trp Arg Leu Cys Thr Lys Trp His His Lys Arg Arg Asp
```

```
1               5                   10                  15
Leu Pro Arg Lys Pro Glu
            20
```

ARTIFICIALLY SYNTHESIZED PEPTIDE

FIELD OF THE INVENTION

The present invention relates to an artificially synthesized peptide useful for delivering biological material. More particularly the invention relates to an artificially synthesized protein for delivering both peptides and DNA.

The rapid developing field of biotechnology, molecular biology and gene therapy requires an efficient delivery system for proteins and nucleic acids as an integral part of research. The major disadvantage of commercially available transfection reagents for proteins and nucleic acids is their cytotoxicity and poor delivery mechanism due to degradation by endosomal enzymes. The delivery system of the present invention has been devised with the objective to target the large protein as well as nucleic acid into cells with minimal cytotoxicity and to deliver biomolecules independent of endocytosis preventing degradation by endosomal enzymes. To achieve the above said, a novel nuclear localization signal and hydrophobic domain identified from infectious Bursal Disease Virus (IBDV) have been, exploited for the first time. Accordingly, the peptide was designed, synthesized and modified; so as to make it free of cytotoxicity and its biological activity was validated experimentally.

BACKGROUND AND PRIOR ARTS

Peptide and nucleotide can serve as best therapeutic but their uses are limited due to non-permeability to cell membrane barrier, which is highly specific. The delivery of protein to the mammalian cells is difficult due to lack of efficient delivery system. The protein transduction domains (PTDs) are the short stretch of amino acids, which can cross the cell membrane and have been tried by binding covalently to the protein to be targeted to the cells, which can be internalized independent of transporter or receptor. The most widely used PTDs for delivery of protein are from Drosophila, the Herpes Simplex Virus structural protein VP22 (Elliot and o'Hare 1997) and Human Immunodeficiency Virus-1 transcription activator T at protein (Frankel and Pabo, 1998). But the main disadvantage of this technology is that it needs covalent coupling of target protein with PTDs or expressing as fusion protein (Schwarze et al., 1999). This increases the additional steps and delays the start of actual experiment. Recent attention has been diverted to develop peptide, which can target the protein or nucleic acids, by noncovalent binding. Therefore, the objective of the present invention was to develop peptide vector, which can deliver both proteins and nucleic acid to variety of cells by exploiting the potential novel nuclear localization signal and a hydrophobic domain from IBDV, with minimal cytotoxicity.

To overcome the above said drawbacks, the present invention is an endeavor to development of a peptide as transfection system for both protein and nucleic acid for non-viral delivery. Although viral vectors remain most efficient gene transfer system in eukaryotic cells, safety concerns regarding their uses in humans and animals has increased the significance for development of non-viral delivery system. Furthermore, non-viral delivery has several advantages over viral systems as simple to use, noninfectious, easy to produce, do not induce specific immune responses and less cytotoxicity. The Applicant has identified for the first time a novel nuclear localization signal (NLS) from Infectious bursal disease virus and it was found to translocate to nucleus, independent of endocytosis, which is an essential feature to develop new successful delivery system. The vector peptide designed using this NLS was found to possess targeting ability of protein to cytoplasm and DNA to nucleus with high transfection ability and minimal cytotoxicity at much higher concentration than required for transfection. This new transfection reagent further has high transfection ability for production of recombinant antigens and direct proteins delivery. Moreover, this single reagent can transfect both protein and nucleic acid with low cost of production.

OBJECTS OF THE PRESENT INVENTION

The main object of the present invention is to develop a carrier to deliver biological material in the cell.

Another object of the present invention is to develop a synthetic peptide based delivery system for biological material.

BRIEF DESCRIPTION OF THE FIGURES

FIG. 1: Vero cell transfected with FITC labeled IgG antibody without peptide for 1 hr as a control FIG. 2: Vero cell transfected with FITC labeled IgG antibody in presence of peptide of the present invention for 1 hr indicates cytoplasmic (C) localization of antibody (Ab) Table 3: Techno-economics of various vehicle used to transport bio-molecules.

FIG. 3: Chicken embryo fibroblast cells transfected with FITC conjugated IgG antibody complexed with peptide of the present invention for 1 hr indicates cytoplasmic (C) localization.

FIG. 4: Targeting FITC labeled oligonucleotides complexed with peptide of the present invention to nucleus of vero cells FIG. 5: Delivery of peptide mediated recombinant GFP reporter plasmid construct to Vero cells, which shows efficient expression of green fluorescent protein (GFP) after 48 hrs in cytoplasm of Vero cells.

FIG. 6: Percent cell viability of complexes composed of peptide:antibody and peptide:GFP plasmid after 20 hrs of transfection

BRIEF DESCRIPTION OF TABLES

Table 1 (a-c): Evaluation of cytotoxicity in mammalian cells (Vero cell line) of the vector peptide and cargo molecule complexes using Cytotox™ kit (Promega)

Table 2: Quantitation of percent cell viability of the vero cells in presence of different concentration of vector peptide Table 3: Comparative Cost Analysis (Indian Rupees)

DETAILED DESCRIPTION OF THE PRESENT INVENTION

Designing and Synthesis of Peptide as Delivery System

Synthetic peptides of length 12 mer and 22 mer corresponding to nonstructural protein of IBDV were synthesized using 'Fmoc' chemistry and purified by reversed phase chromatography using $C_{18}$ column. To develop ideal peptide based delivery system a series of modifications in native 22 mer peptide have been incorporated like addition of hydrophobic groups such as tryptophan instead of cysteine to improve membrane transduction ability and DNA/protein binding capacity, as well as to avoid non-specific crosslinking of carrier peptide with cargo molecule through S—S bond between cysteine residues. Moreover, addition of tryptophan can facilitate hydrophobic interactions with proteins during delivery into cells.

It was observed that 22-mer peptide possesses DNA and protein carrying capacity but showed cytotoxicity at higher concentration, i.e., at 100 μM. Therefore, a modification was introduced in between C-terminal hydrophilic and N-terminal hydrophobic domains of 22-mer peptide resulting into a peptide of 25 amino acids, which demonstrated negligible cytotoxicity even up to 100 μM concentration and can serve as ideal delivery system. The peptide sequence is as follows:

```
                                            (SEQ ID NO: 1)
TPWWRLWTKWSQPHHKRRDLPRKPE,
```

Experimental Analysis:

The designed peptide was synthesized and used as general transfection reagent for vero cells and chicken embryo fibroblast primary cells. This designed peptide as a vector was checked for its ability of internalization at both 37° C. as well as 4° C., and was found to be capable of internalizing independent of endocytosis pathway. Further, different biomolecules were transfected by complexing them with different concentrations of peptide in vero cells and chicken embryo fibroblast primary cultured cells. As compared to control (FIG. 1), efficient delivery of complete IgG antibody was observed within an hour of transfection in vero cells (FIG. 2) and Chicken Embryo Fibroblast cells (FIG. 3) by fluorescent microscopy. This vector peptide could target FITC labeled oligonucleotides completely to nucleus in less than 2 hrs (FIG. 4) and was further found to be capable of internalizing even a plasmid construct having a reporter gene to cell for its expression to produce desired protein in cells (FIG. 5). The cell viability up to 98% was observed at 100 μM concentration of peptide complexed with antibody and plasmid (FIG. 6), suggesting that this is an ideal system for transfection of both proteins and nucleic acids with minimal cytotoxicity. The strong binding with nucleic acid was confirmed by gel shift assay and cytotoxicity assay in vero cells using standard kits. Stability of DNA complexed with peptide in the presence of 10% serum and nucleases was confirmed by serum protection assay and nuclease protection assay, respectively. The Applicant is able to successfully deliver antibodies of size as big as 180 kd. Further recombinant plasmid DNA of size 3 kilo base having GFP gene insert was successfully delivered into cell and demonstrated the expression of the GFP protein. It was observed that the binding is through noncovalent interactions with the cargo molecule of the present invention. In case of genetically engineered plasmid vector through electrostatic interactions between phospate and basic residues of the peptide and hydrophobic interactions play vital role to take the cargo across the cell membrane barriers. The release of the protein or DNA molecule as the case may be is released by the carrier molecule of the present invention inside the cell or nucleus due to changes in the environment i.e. dielectric constant inside the cell which is entirely different from outside To access the applicability of this transfection reaction as a viable technology the cytotoxicity of the peptide was evaluated using Cytotox™ kit (Promega) the cytotoxicity data is given in the table.

| | Vector peptide concentration (in μM) | | |
|---|---|---|---|
| Expt. No. | 0.5 | 10 | 100 |
| Table 1(a) OD at 492 nm (Vector peptide alone) | | | |
| 1. | 0.385 | 0.372 | 0.439 |
| 2. | 0.343 | 0.326 | 0.416 |
| 3. | 0.324 | 0.319 | 0.412 |
| Table 1(b) OD at 492 nm (Vector peptide complexed with antibody) | | | |
| 1. | 0.366 | 0.387 | 0.368 |
| 2. | 0.377 | 0.404 | 0.394 |
| 3. | 0.343 | 0.428 | 0.419 |
| Table 1 (c) OD at 492 nm (Vector peptide complexed with plasmid) | | | |
| 1. | 0.374 | 0.353 | 0.386 |
| 2. | 0.361 | 0.336 | 0.416 |
| 3. | 0.367 | 0.394 | 0.408 |

Positive Control:

OD at 492 nm of max Lactate dehydrogenase are –3.086, 3.079 and 3.176

Negative Control:

OD at 492 nm of as GMEM with 5% serum are –0.357, 0.382 and 0.371

TABLE 2

| | Vector peptide concentration (in μM) | | |
|---|---|---|---|
| Cells viability assays | 0.5 | 10 | 100 |
| Peptide alone | 99.02% | 98.82% | 95.70% |
| Peptide complex with antibody | 99.27% | 97.70% | 98.24% |
| Peptide complex with plasmid | 99.10% | 99.30% | 97.90% |

TABLE 3

| Product | Manufacturer | For delivery of | Price per reaction (Approximate Rs.) |
|---|---|---|---|
| Vector Peptide | Our designed Peptide as Transfection reagent | Protein Oligonucleotides Plasmid DNA | 12/- 6/- 24/- |
| CHARIOT | Active Motif Inc. Carlsbad, CA | Protein | 187/- |
| Poly Fect | QIAGEN, Germany | DNA | 140/- |
| SuperFect | QIAGEN, Germany | DNA | 253/- |
| Lipofectamine | Life Technologies, USA | DNA | 292/- |
| EXCORT ™ II | SIGMA, USA | DNA | 115/- |

The above table indicates the comparison of approximate cost of commercially available transfection reagents, most commonly used, with our designed transfection system. The values are for 6-well plate (35 mm dish) with 2 ml final volume of medium.

Protocol for the Use of Invented Vector Peptide as Transfection Reagent

Dissolve vector peptide in PBS or 'milli Q' water to desired concentration

↓

Take 100 µl of PBS or cell culture medium in microtube.

↓

Add desired quantity of proteins/nucleic acids

↓

Incubate with vector peptide at 37° C. for 30 min.

↓

Overlay this complex to cultured cells using medium without serum.

↓

Internalization of oligonucleotide and protein will take 1 hr at 37° C..

For plasmid DNA, incubate with peptide for 2 hrs and continue incubation for desired time to get expression.

Advantages of this Technology/Invention a. It has minimized the problem of cytotoxicity during transfection.
b. Simple protocol for use.
c. Efficient and quick delivery of proteins and nucleic acids just by mixing with peptide.
d. Synthetic peptides under anhydrous condition are stable at room temperature. So no need to maintain the cold chain as recommended for commercial available transfection reagents.
e. Delivery by endocytosis independent pathway, so delivery is much more efficient.
f. A single peptide could be used as transfection reagent for both protein and nucleic acid.
g. This can be cost effective and cheaper than other commercially available delivery systems (Please refer Table 3).
h. It increases the stability of biomolecules during delivery by forming strong complexes. The peptide protects DNA in the presence of serum and Dnase.
i. Strong DNA binding ability of peptide makes it as ideal candidate for DNA transfection.
j. It could transfect into wide variety of cells, including primary cultures.
k. It is insensitive to presence of antibiotics in medium as compared to commercial lipid based transfection reagents as Lipofectamine (Life Technologies, USA).
l. It is safe to use in any lab as handling of harmful or toxic reagents is not involved in experiments.

REFERENCES

1. Elliot, G. and O'Hare, P. (1997). Intracellular trafficking and protein delivery by a herpes virus structural protein. *Cell,* 88: 223-233.
2. Frankel, A. D. and Pabo, C. O. (1998). Cellular uptake of Tat protein from human deficiency virus. *Cell,* 55: 1189-1193.
3. Schwarze, S. K., Ho, A., Vicero-Akabani, A. and Dowdy, S. F. (1999). In vivo protein production: delivery of biologically active protein into the mouse. *Science.* 285: 1569-1572.

We claim:

1. An artificially synthesized peptide for delivering bio-molecules into a cell comprising SEQ ID NO: 1.

2. The artificially synthesized peptide of claim 1, which delivers bio-molecules into a cell independent of the endocytosis pathway.

3. A recombinant transfection system comprising:
a peptide comprising SEQ ID NO: 1, and
a bio-molecule,
wherein the peptide forms a complex with the bio-molecule and delivers the bio-molecule into a cell or nucleus without degradation of the bio-molecule.

4. The recombinant transfection system of claim 3, wherein the bio-molecule is a nucleic acid and/or protein.

5. A method of delivering a bio-molecule into a cell without inducing an immune response or cytotoxicity, comprising:
incubating a peptide comprising SEQ ID NO: 1 and a bio-molecule at 37° C. such that they form a complex; and
overlaying the complex on the cell such that the complex is internalized into the cell.

6. The method of claim 5, wherein the bio-molecule is a nucleic acid and/or protein.

7. A kit for delivering bio-molecules into a cell, said kit comprising:
a peptide comprising SEQ ID NO: 1, and
an instruction manual.

8. The method of claim 5, wherein the bio-molecule is protected from degradation.

9. The method of claim 5, wherein the bio-molecule is released inside the cell due to changes in a dielectric constant.

10. The method of claim 5, wherein the cell is a primary cell.

11. The method of claim 5, wherein the cell is an embryonic cell.

12. The artificially synthesized peptide of claim 1, which targets protein to the cytoplasm.

13. The artificially synthesized peptide of claim 1, which targets DNA to the nucleus.

14. The recombinant transfection system of claim 3, wherein the peptide and the bio-molecule form a complex through noncovalent interactions.

15. The recombinant transfection system of claim 3, wherein the bio-molecule is a plasmid.

16. An artificially synthesized peptide consisting of SEQ ID NO: 1.

17. A recombinant transfection system comprising:
the artificially synthesized peptide of claim 16, and
a bio-molecule,
wherein the peptide forms a complex with the bio-molecule and delivers the bio-molecule into a cell or nucleus without degradation of the bio-molecule.

18. A kit for delivering bio-molecules into a cell, said kit comprising:
the artificially synthesized peptide of claim 16, and
an instruction manual.

19. A method of delivering a bio-molecule into a cell without inducing an immune response or cytotoxicity, comprising:
incubating a peptide consisting of SEQ ID NO: 1 and a bio-molecule at 37° C. such that they form a complex; and
overlaying the complex on the cell such that the complex is internalized into the cell.

20. The method of claim 19, wherein the bio-molecule is a nucleic acid and/or protein.

* * * * *